(12) United States Patent
Kramer et al.

(10) Patent No.: US 7,286,872 B2
(45) Date of Patent: Oct. 23, 2007

(54) METHOD AND APPARATUS FOR MANAGING DATA FROM MULTIPLE SENSING CHANNELS

(75) Inventors: Karen M. Kramer, Stillwater, MN (US); Doug Gifford, Ham Lake, MN (US); Douglas J. Brandner, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 689 days.

(21) Appl. No.: 10/680,731

(22) Filed: Oct. 7, 2003

(65) Prior Publication Data

US 2006/0058850 A1    Mar. 16, 2006

(51) Int. Cl.
*A61N 1/00* (2006.01)
(52) U.S. Cl. .......................................... 607/2
(58) Field of Classification Search ............... 600/508, 600/509, 510, 513, 544, 546; 607/2, 4, 5, 607/9
See application file for complete search history.

(56) References Cited

U.S. PATENT DOCUMENTS

| 4,223,678 | A | 9/1980 | Langer et al. |
|---|---|---|---|
| 4,316,249 | A | 2/1982 | Gallant et al. |
| 4,407,288 | A | 10/1983 | Langer et al. |
| 4,527,567 | A | 7/1985 | Fischler et al. |
| 4,531,527 | A | 7/1985 | Reinhold, Jr. et al. |
| 4,549,552 | A | 10/1985 | Groch et al. |
| 4,596,255 | A | 6/1986 | Snell et al. |
| 4,601,291 | A | 7/1986 | Boute et al. |
| 4,791,936 | A | 12/1988 | Snell et al. |
| 4,809,697 | A | 3/1989 | Causey, III et al. |
| 4,825,869 | A | 5/1989 | Sasmor et al. |
| 4,944,298 | A | 7/1990 | Sholder |
| 4,964,410 | A | 10/1990 | Leahey et al. |
| 4,979,506 | A | 12/1990 | Silvian |
| 5,209,228 | A | 5/1993 | Cano et al. |
| 5,217,021 | A | 6/1993 | Steinhaus et al. |
| 5,311,874 | A | 5/1994 | Baumann et al. |

(Continued)

FOREIGN PATENT DOCUMENTS

EP    0565084    10/1993

(Continued)

OTHER PUBLICATIONS

"International Search Report for corresponding PCT Application No. PCT/US2004/042269", (Mar. 31, 2005),5 pgs.

(Continued)

*Primary Examiner*—Carl Layno
*Assistant Examiner*—Jon-Eric Morales
(74) *Attorney, Agent, or Firm*—Schwegman, Lundberg & Woessner, P.A.

(57) ABSTRACT

An implantable medical device comprising a plurality of implantable electrodes to sense the electrical activity and an implantable medical device coupled to the electrodes. The implantable medical device includes a plurality of sense amplifiers in communication with the electrodes to produce analog electronic signals representative of the electrical activity and a programmable sampler. The implantable medical device also includes a controller that programmably enables the sampler to selectively sample the electronic signals. The controller also includes memory in communication with the controller for storage of the sample values. The controller configures the memory based on the programmable sampling.

52 Claims, 6 Drawing Sheets

U.S. PATENT DOCUMENTS

| | | | |
|---|---|---|---|
| 5,312,446 A | 5/1994 | Holschbach et al. | |
| 5,357,969 A | 10/1994 | Herleikson | |
| 5,391,188 A | 2/1995 | Nelson et al. | |
| 5,402,794 A | 4/1995 | Wahlstrand et al. | |
| 5,404,880 A | 4/1995 | Throne | |
| 5,413,594 A | 5/1995 | Williams | |
| 5,417,714 A | 5/1995 | Levine et al. | |
| 5,431,692 A | 7/1995 | Hansen et al. | |
| 5,476,485 A | 12/1995 | Weinberg et al. | |
| 5,487,755 A | 1/1996 | Snell et al. | |
| 5,507,786 A | 4/1996 | Morgan et al. | |
| 5,511,553 A | 4/1996 | Segalowitz | |
| 5,513,645 A | 5/1996 | Jacobson et al. | |
| 5,549,654 A * | 8/1996 | Powell | 607/32 |
| 5,578,063 A | 11/1996 | Bocek et al. | |
| 5,591,214 A | 1/1997 | Lu | |
| 5,603,331 A | 2/1997 | Heemels et al. | |
| 5,609,615 A | 3/1997 | Sanders et al. | |
| 5,628,776 A | 5/1997 | Paul et al. | |
| 5,653,737 A | 8/1997 | van Lake | |
| 5,683,431 A | 11/1997 | Wang | |
| 5,709,712 A | 1/1998 | Paul et al. | |
| 5,722,999 A | 3/1998 | Snell | |
| 5,732,708 A | 3/1998 | Nau et al. | |
| 5,759,196 A | 6/1998 | Hess et al. | |
| 5,782,890 A | 7/1998 | Wahlstrand et al. | |
| 5,792,207 A | 8/1998 | Dietrich | |
| 5,814,083 A * | 9/1998 | Hess et al. | 607/14 |
| 5,891,178 A | 4/1999 | Mann et al. | |
| 5,904,708 A | 5/1999 | Goedeke | |
| 5,908,392 A | 6/1999 | Wilson et al. | |
| 5,925,067 A | 7/1999 | Lu | |
| 5,974,341 A | 10/1999 | Er et al. | |
| 5,978,707 A | 11/1999 | Krig et al. | |
| 6,016,442 A | 1/2000 | Hsu et al. | |
| 6,016,446 A | 1/2000 | Belalcazar | |
| 6,045,513 A * | 4/2000 | Stone et al. | 600/508 |
| 6,067,471 A | 5/2000 | Warren | |
| 6,076,015 A * | 6/2000 | Hartley et al. | 607/20 |
| 6,091,990 A | 7/2000 | Hsu et al. | |
| 6,108,577 A | 8/2000 | Benser | |
| 6,112,117 A | 8/2000 | KenKnight et al. | |
| 6,128,528 A * | 10/2000 | Ericksen et al. | 607/2 |
| 6,243,606 B1 | 6/2001 | Mann et al. | |
| 6,263,244 B1 | 7/2001 | Mann et al. | |
| 6,308,095 B1 | 10/2001 | Hsu et al. | |
| 6,311,089 B1 | 10/2001 | Mann et al. | |
| 6,312,378 B1 * | 11/2001 | Bardy | 600/300 |
| 6,400,985 B1 | 6/2002 | Amely-Velez | |
| 6,427,083 B1 | 7/2002 | Owen et al. | |
| 6,442,428 B1 | 8/2002 | Shankar et al. | |
| 6,449,504 B1 | 9/2002 | Conley et al. | |
| 6,459,929 B1 | 10/2002 | Hopper et al. | |
| 6,459,934 B1 | 10/2002 | Kadhlresan | |
| 6,535,763 B1 | 3/2003 | Hiebert et al. | |
| 6,625,488 B2 | 9/2003 | Poore et al. | |
| 6,636,765 B2 | 10/2003 | Amely-Velez | |
| 6,941,167 B2 | 9/2005 | Stahmann | |
| 2002/0065540 A1 | 5/2002 | Lebel et al. | |
| 2002/0077859 A1 | 6/2002 | Stahmann et al. | |
| 2002/0082509 A1 | 6/2002 | Vanderlinde et al. | |
| 2002/0107550 A1* | 8/2002 | Amely-Velez | 607/9 |
| 2002/0151809 A1 | 10/2002 | Conley et al. | |
| 2003/0158492 A1* | 8/2003 | Sheldon et al. | 600/508 |
| 2004/0167416 A1* | 8/2004 | Lee | 600/513 |
| 2004/0225332 A1* | 11/2004 | Gebhardt et al. | 607/17 |
| 2005/0137627 A1 | 6/2005 | Koshiol et al. | |

FOREIGN PATENT DOCUMENTS

| | | |
|---|---|---|
| EP | 0711531 | 5/1996 |
| EP | 0850661 | 7/1998 |
| EP | 1245248 A2 | 10/2002 |
| WO | WO2005/063118 | 7/2005 |

OTHER PUBLICATIONS

Tanenbaum, A. S., "Computer Networks", *Prentice-Hall, Inc., Englewood Cliffs*, NJ, (1981), 125-128.

* cited by examiner

METHOD AND APPARATUS FOR MANAGING DATA FROM MULTIPLE SENSING CHANNELS

TECHNICAL FIELD

This patent application relates to devices that communicate with implantable medical devices and, in particular, to a system and method for retrieving data collected by an implantable medical device.

BACKGROUND

Implantable medical devices (IMDs) are devices designed to be implanted into a patient. Some examples of these devices include cardiac rhythm management devices such as implantable pacemakers and implantable cardioverter defibrillators (ICDs). The devices are used to treat patients using electrical therapy and to aid a physician in patient diagnosis through internal monitoring of a patient's condition. The devices include electrical leads in communication with sense amplifiers to monitor electrical activity within a patient and often include sensors to monitor other internal patient parameters. In general, the sensors convert sensed internal parameters into electrical signals. The electrical signals monitored within the patient and the electrical signals from the sensors can be quantified by analog-to-digital converters and stored in the IMD as data.

Implantable medical devices are able to communicate with external devices using wireless communication methods such as radio frequency (RF) or mutual inductance. The external devices are often external programmers that use wireless communication to change performance parameters in the implantable device. The implantable device also transmits the stored data to an external device using the wireless communication.

As technology used in the implantable medical devices increases, the devices collect data from multiple leads and multiple sensors. Potentially, this results in large amounts of data to be collected by the implantable device and transmitted to the external device. Additionally, the data may be collected from different types of sensors at different rates, or processing may be done on the collected data by the implantable device before the data is transmitted. This complicates the task of making efficient use of resources within the implantable device such as memory and the wireless communication interface. It also results in the data being available from the implantable device at different times and complicates the task of data management for caregivers. What is needed is an improved method of managing data available from implantable medical devices.

SUMMARY

This document discusses a device, system and method for dynamic configuration of memory space and data acquisition channels within an implantable device.

The device comprises a plurality of implantable electrodes adaptable for sensing the heart's electrical activity and an implantable medical device (IMD) coupled to the electrodes. The IMD includes a plurality of sense amplifiers coupled to the electrodes to produce analog electronic signals representative of the electrical activity and a programmable sampler coupled to the sense amplifiers to sample the electronic signals. The IMD also includes a controller coupled to the programmable sampler. The controller programmably enables the sampler to selectively sample the electronic signals. The IMD also includes configurable memory coupled to the controller for storage of the sample values. The controller configures the memory based on the programmable sampling.

The system comprises an IMD and an external device to communicate with the IMD. The IMD includes a plurality of sense channels adapted to provide analog electronic signals representative of the electrical activity and at least one analog-to-digital (A/D) converter coupled to the sense channels to convert the signals into digital data representative of the signals. The IMD also includes a controller coupled to the A/D converter to sample data provided by the sense channels and a memory coupled to the controller. The controller initiates sampling of at least one sense channel in response to a request for data from at least one user. The controller also predetermines a configuration of a portion of the memory into a plurality of buffers to transfer the sampled sense channel data from the at least one A/D converter to a configured buffer. The IMD further includes a telemetry circuit coupled to the controller to transmit data. The external device provides requests to sense types of electrical activity from at least one user to the IMD. The external device retrieves the requested data from the implantable medical device.

The method comprises sensing electrical activity at a plurality of locations of a heart as a result of a request from at least one user, converting the sensed activity into data suitable for storage in memory, and programmably configuring a memory into a plurality of buffers to accept the data based on a number of requests and types of sensed activity requested by the user.

This summary is intended to provide an overview of the subject matter of the present application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural changes may be made without departing from the scope of the present invention.

The present application discusses a method of dynamically configuring memory space and data acquisition channels within an implantable device.

Figure 1:
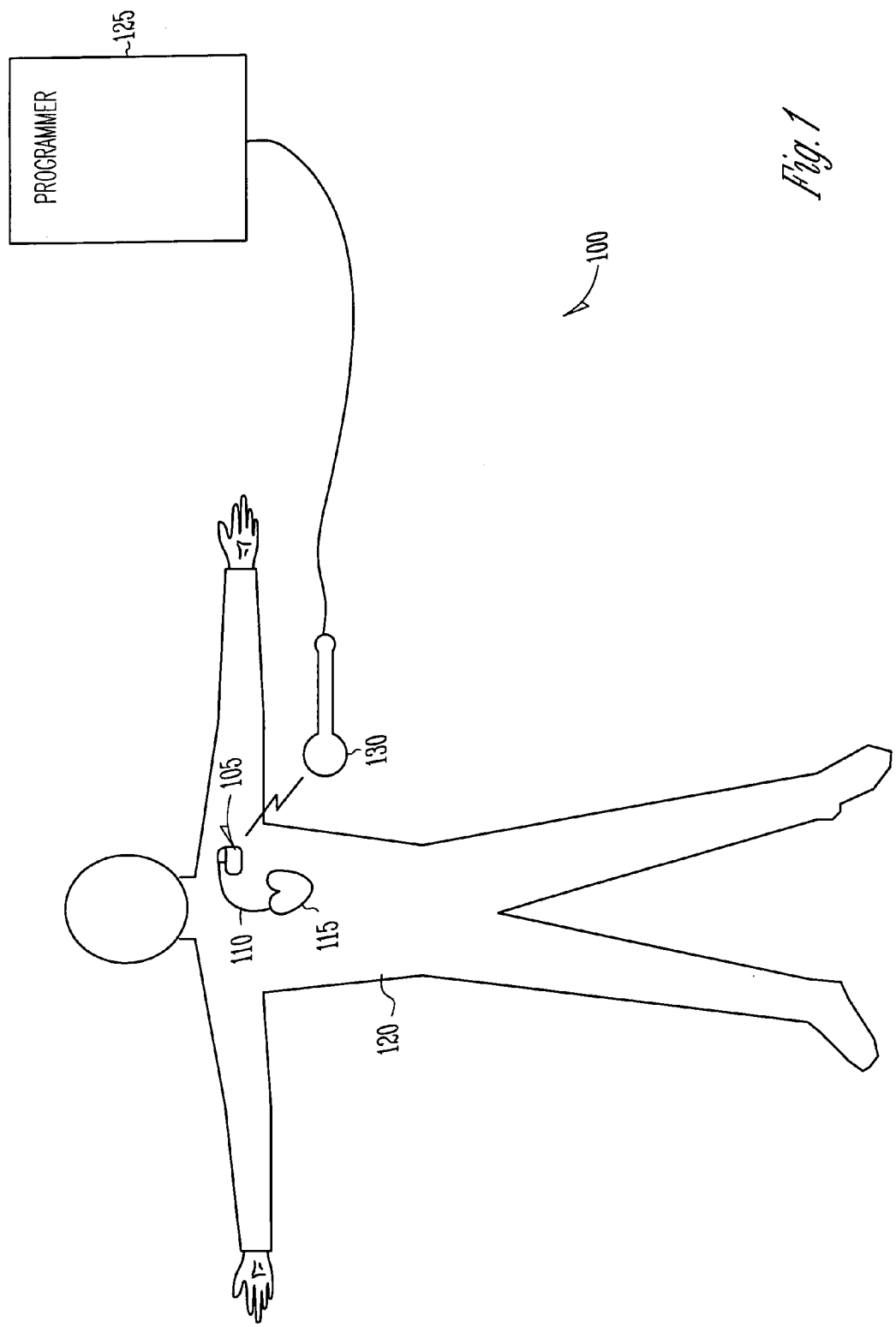
FIG. 1 is an illustration of a system using an implantable medical device.

FIG. 1 is an illustration of an embodiment of a system 100 that uses an implantable medical device 105. The system 100 shown is of one embodiment of portions of a system 100 for treating cardiac arrhythmia where the implantable device is a pulse generator (PG) 105 coupled by a cardiac lead 110, or additional leads, to a heart 115 of a patient 120. Implantable PG 105 can take the form of a pacemaker, a defibrillator, or a defibrillator that includes pacing capability, but the present subject matter applies to any implantable device that is able to collect, store and transmit data while implanted in a patient 120. System 100 also includes an external programmer 125 that provides for wireless communication with the implantable PG 105 using telemetry device 130.

Figure 2:
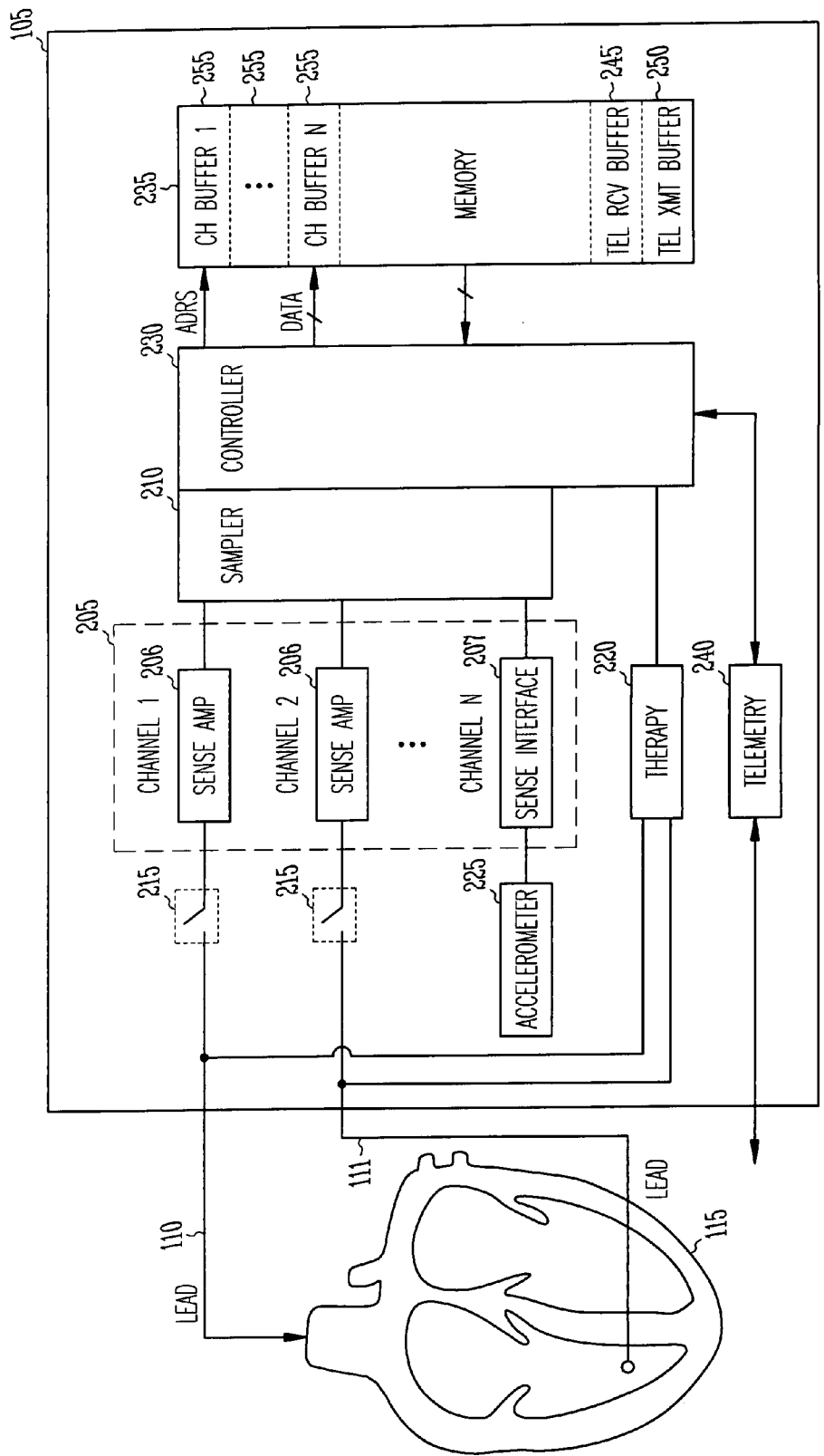
FIG. 2 is an illustration of an embodiment of an implantable medical device.

FIG. 2 is a block diagram of an implantable device that is a PG 105 coupled to electrodes attached to a heart 115 by cardiac leads 110, 111. The PG 105 includes a therapy circuit 220 for delivering electrical pacing therapy or high-voltage defibrillation shock therapy through the electrodes. The PG 105 also includes a hermetically sealed housing enclosing the device that is sometimes referred to as a can. In one embodiment, the PG 105 uses the housing as an electrode. The PG 105 also includes interface circuits 205 for sensing electrical signals. The interface circuits include sense amplifiers 206 to detect electrical activity on the leads 110, 111. The sensed activity on the leads 110, 111 is used to determine appropriate therapy and to generate analog electrical signals suitable for sampling by the programmable sampler 210. Sense amplifiers can also be included to sense signals between a lead 110, 111 and the housing. The PG 105 further includes switches 215 to electrically disconnect, or blank, the sense amplifiers 206 from the therapy circuit during therapy delivery to avoid damaging the sense amplifiers. Various embodiments of the system 100 include additional electrodes. For example, cardiac leads 110, 111 can be bipolar leads comprising tip and ring electrodes where the therapy pulse is delivered from the tip to the ring.

In further embodiments, the PG 105 also includes sensor interface circuits 207 to sample sensors such as the accelerometer 225 shown in the figure. In various embodiments the sensors are internal to the PG 105 or implanted external to the PG 105. The interface circuits for sensors include filter circuits, amplifier circuits, impedance matching circuits, and the like, and are used to generate signals appropriate for sampling by the sampler 210. The sources of the sampled data, such as the leads 110, 111 and sensors 225 together with the corresponding interface circuits 205 are sometimes referred to as data channels or sense channels.

Figure 3:
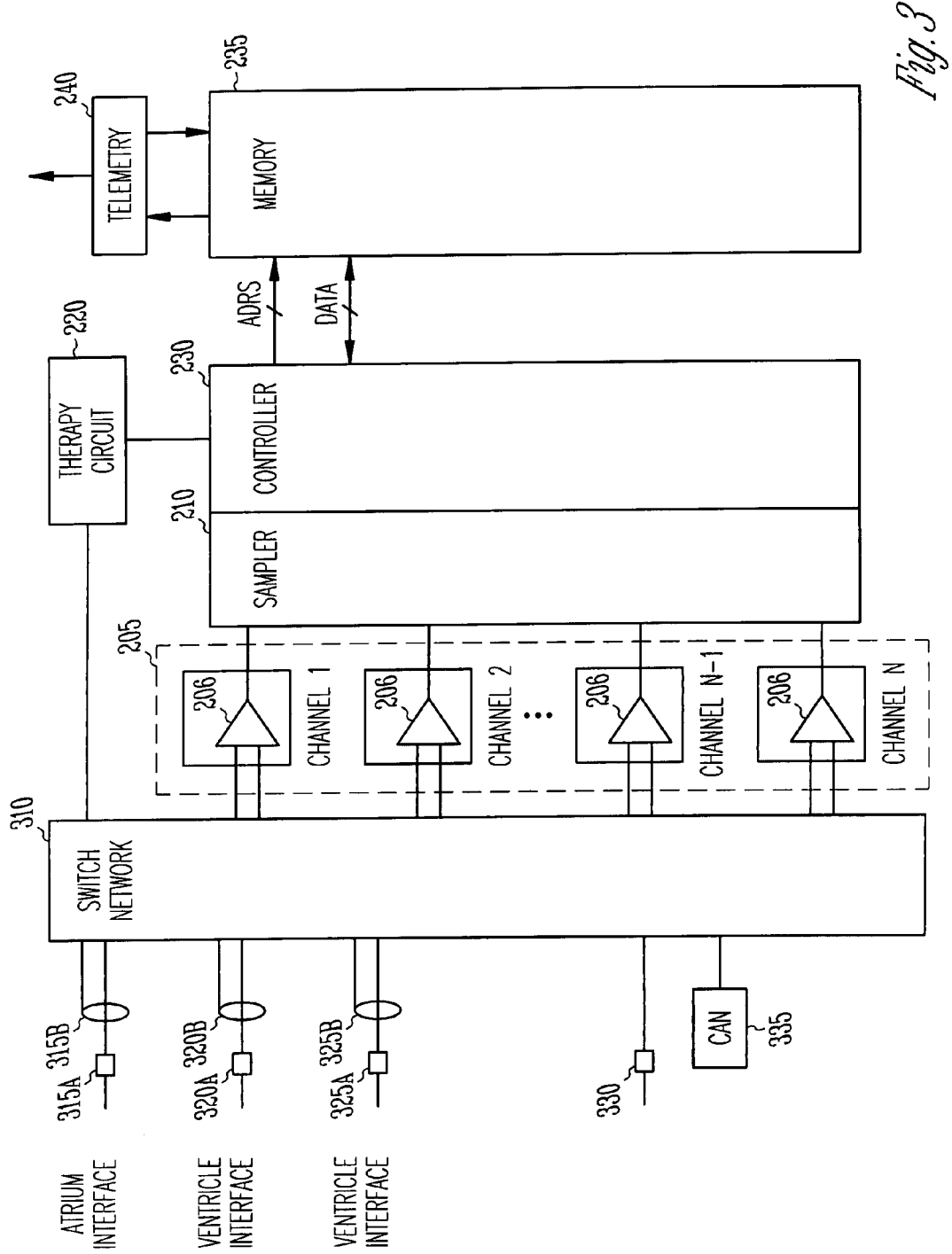
FIG. 3 is an illustration of another embodiment of an implantable medical device.

FIG. 3 shows another embodiment of an implantable medical device that includes bipolar leads 315, 320, 325. The bipolar lead 315 that interfaces to an atrium of a heart 115 includes a tip electrode 315a and a ring electrode 315b. Typically the implanted device senses voltages on the lead 315 between the tip electrode 315a and the ring electrode 315b, or delivers electrical therapy between the tip electrode 315a and ring electrode 315b. The embodiment also includes a switching network 310 that allows sensing between any two electrodes in the system 100. For example, switching network 310 is able to switch tip electrode 315a and tip electrode 325a onto the inputs of one of the sense amplifiers 206. The switching network 310 is also able to place tip electrode 330 and the can electrode 335 onto the inputs of a sense amplifier. Sensing signals between a tip electrode 330 and a can electrode 335 is useful to obtain a sample of an evoked response signal. When measuring an evoked response, the sense amplifiers 206 are not blanked during low energy pacing therapy. When the source of the sampling is such a signal sensed between any two electrodes in the system, this source is sometimes referred to as a utility channel.

Returning to FIG. 2, the sampler 210 is programmable in that sampling of individual signals can be enabled. In one embodiment enabling includes selecting the output of the sense channel for sensing. In another embodiment, enabling includes applying power to the sense channel if it is selected for sampling and removing power if it is not selected. The sampler 210 converts the analog signals into digitized samples suitable for storage in memory within the implantable device. In one embodiment, the sampling is done using an analog-to-digital (A/D) converter. The sampler 210 can also be programmed to change the rate at which data is collected. For example, cardiac lead 111 is shown placed in a ventricle of a heart 115. A sense amplifier 206 attached to the lead generates signals suitable for sampling to create an electrogram of the electrical activity in the ventricle. In one embodiment, sampler 210 is programmable to sample ventricular data at either 200 Hz or 400 Hz. The 400 Hz sampling creates an electrogram of the ventricular signals with increased fidelity over the 200 Hz sampling and generates data at twice the rate. In another embodiment, accelerometer data is sampled at 100 Hz. Other sampling rates are within contemplation of the present application.

Controller 230 enables sampling of the signals and controls storage of the digitized samples in memory 235. The digitized data can also be used to produce processed data. In one embodiment the processed data is produced using filtering. In another embodiment, the processing is done using digital signal processing (DSP). As an example, sampled signals obtained from an accelerometer can be filtered data or unfiltered data (sometimes referred to as "raw" data). In yet another embodiment, the processing includes functions useful to calculate minute ventilation (MV), or minute volume, from sensed signals. Examples of functions useful in calculating MV can be found in U.S. Pat. No. 6,076,015, "Rate Adaptive Cardiac Rhythm Management Device Using Transthoracic Impedance," Hartley et al, which is incorporated herein by reference.

The various types of data discussed above are accumulated at different rates. This difference may be due to the sampler being programmed to a different sampling rate, or due to processing of the data. In one embodiment, filtered or unfiltered data is available from the sense channels at 100 Hz, 200 Hz or 400 Hz, and processed data, such as MV data, is available at 20 Hz.

The PG 105 further includes a telemetry circuit 240 for wireless communication with an external device. The telemetry circuit 240 is used to receive programming information from the external device into the controller 230. Data is received into the telemetry circuit 240 and moved into the telemetry receive buffer 245 before being moved to a memory location. In this way, the external device can change programming in the PG 105. Telemetry circuit 240 is also used to transmit data to the external device. To transmit data, controller 230 reads data from memory 235, modifies the data for transmission and writes it into a telemetry transmit buffer 250. The controller 230 then sends the data to the telemetry circuit 240 for transmission at a rate dictated by the telemetry communication protocol. The external device is used to display the information for the caregiver.

Figure 4:
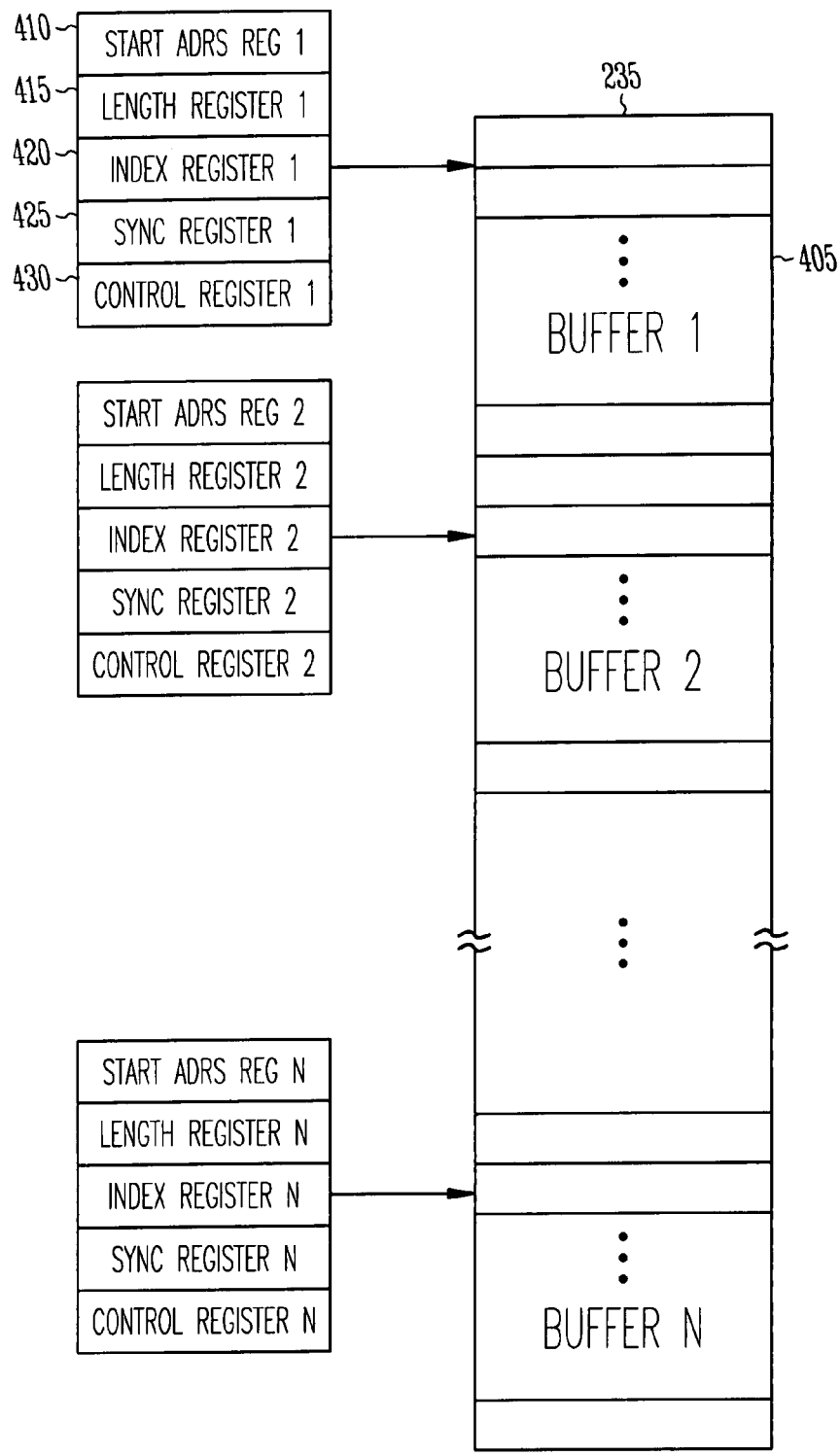
FIG. 4 is a block diagram of an embodiment of configurable buffers for use within an implantable medical device.

When data collection from the channels is enabled, memory 235 is configured into buffers 255 by the controller 230 to store the collected data. The controller 230 configures the number of buffers 255 and the sizes of the buffers. FIG. 4 shows a block diagram of one embodiment of configurable buffers for use within an implantable medical device. Memory 235 is configured into N buffers 405. Data collected from sampling the sensed signals is stored in the configured buffers 405 at the rate it is collected. A configured buffer 405 includes a number of registers.

A start address register 410 and a length register 415 reserve the location and size of the buffer 405 in memory 235. An index register 420 is incremented after data is written to the buffer 405 to point to the location for the next data sample in the buffer 405. An index register 420 is useful to reduce the chance of gaps occurring in the data within the buffer. In one embodiment, the buffers 405 are circular buffers and the index register rolls over back to the beginning of the buffer when the register is incremented beyond the end of the buffer. A rollover indicator is used to indicate when this occurs. In another embodiment, the buffers 405 are linear buffers. A synchronization, or sync, register 425 contains a timestamp used to indicate a timing relationship among the data in several buffers so that the data from multiple buffers can be aligned for display. In one embodiment, the timestamp is updated whenever the index register 420 returns to the beginning of the buffer. A control register 430 indicates the source of the data as a specific type. In one embodiment, the control register 430 also indicates the rate at which the data is being collected from the sense channel.

A series of tables are used to monitor the configurations of buffers 405. In one embodiment, the tables reside in firmware. In another embodiment, the tables reside in software. In yet another embodiment, the tables reside in a combination of software and firmware.

In one embodiment, an initial configuration is created after system reset. This configuration is stored in a hardware buffer length table that contains the length of the identified buffers after reset. The starting address of the buffers is determined by the controller. One embodiment of a hardware buffer length table is shown below in Table 1.

Creating an initial configuration at system reset ensures that buffers are available to collect data required by key tasks such as history storage or real time transmission of data via telemetry. In one embodiment, the size of the buffer for a telemetry task is allocated to accommodate a difference between a data collection rate and a telemetry transmission rate.

TABLE 1

Hardware Buffer Length Table

| Buffer No. | Configurable Length (bytes) |
|---|---|
| 1 | 3000 |
| 2 | 3000 |
| 3 | 3000 |
| 4 | 3000 |
| 5 | 400 |
| 6 | 400 |
| 7 | 550 |
| . . . | . . . |
| N | 550 |

In addition to ensuring that enough buffer space is available for key tasks, some buffers need to be reserved for the key tasks. In one embodiment, the need to reserve a buffer is allocated by a priority. Priority can be based upon various criteria such as the rate on which data is collected. Buffers 405 are reserved by a reserved lead configuration table. This table is used in conjunction with the hardware buffer length table to configure the N buffers 405. One embodiment of a reserved lead configuration table is shown below in Table 2. The table is indexed by the buffer number, or ID, and includes a code for the indicated reserved channel.

TABLE 2

Reserved Lead Configuration Table

| Buffer No. | Reserved Channel (Code) |
|---|---|
| 1 | Right Ventricle (200 Hz) |
| 2 | Left Ventricle (200 Hz) |
| 3 | Right Atrium (200 Hz) |
| 4 | Shock Lead (200 Hz) |
| 5 | Right Ventricle (400 Hz) |
| 6 | Shock Lead (400 Hz) |
| 7 | Open |
| . . . | . . . |
| N | Open |

The control register 430 uses a channel configuration table to indicate the source of the data. The table stores an enumerated value used as an index into the table. One embodiment of a channel configuration table is shown below in Table 3.

TABLE 3

Channel Configuration Table

| Channel Type (Enumerated Value) | Hardware Code | Cycles per Sample | Samples per 16-bit word |
|---|---|---|---|
| Type 1 | Code 1 | No. Clock Cycles | 0–2 |
| Type 2 | Code 2 | No. Clock Cycles | 0–2 |
| . . . | . . . | . . . | . . . |
| Type M | Code M | No. Clock Cycles | 0–2 |

Corresponding to each enumerated value of a channel type is a hardware code to be written into the control register, a number of clock cycles required per sample and the number of samples per sixteen-bit word. The hardware code is a value that depends on the hardware interface and enables the requested sense channel or channels. The cycle per sample indicates to the controller 230 how often data is available for transfer to a buffer 405. The cycles per sample is also used along with the sync counter to align one buffer of data with the data of another buffer collecting data at a different rate. The number of samples is the number of digitized sample values that are to be stored per sixteen-bit word of memory. In one embodiment, data samples are collected in eight-bit or twelve-bit words depending on the source of the sampled data. Data words of different sizes, such as four or sixteen-bit words for example, are within contemplation of the subject matter of the present application. An example of an implementation of the channel configuration table is shown below in Table 4.

Table 4 shows entries for the left and right ventricles and right atrium at 200 Hz and 400 Hz. Eight bit values are stored for samples taken at 200 Hz and twelve bit values are stored for samples taken at 400 Hz. The example in Table 4 also includes entries for sampling of a shock lead. Data is not sampled on shock leads during defibrillation shock therapy to avoid damaging the sense amplifiers. Table 4 also shows entries for a utility measurement, evoked response measurement, both raw and filtered accelerometer sampling, and both raw and filtered MV sampling. The Table further shows that in one embodiment, the channel configuration table can be used to turn off a specific channel.

The controller 230 can change the buffer configuration after system reset as a result of receiving requests for types of data. A request for data is made when an application is started that needs a type of data. The controller 230 can change the configuration by configuring additional buffers 405 or re-allocating existing buffers 405 by updating the contents of the start address register 410, the length register 415, the index register 420, the sync register 425 and the control register 430.

Because the buffers are configured with a start address register 410 and length register 415, it is not necessary for one buffer to follow sequentially right after another buffer in memory. The buffers may appear in any order and reside anywhere in memory 235.

TABLE 4

Channel Configuration Table Example

| Channel Type (Enumerated Value) | Hardware Code | Cycles per Sample | Samples per 16-bit word |
|---|---|---|---|
| Channel Off | | 0 | 0 |
| Right Atrium 200 Hz | | 2 | 2 |
| Right Atrium 400 Hz | | 1 | 1 |
| Right Ventricle 200 Hz | | 2 | 2 |
| Right Ventricle 400 Hz | | 1 | 1 |
| Left Ventricle 200 Hz | | 2 | 2 |
| Left Ventricle 400 Hz | | 1 | 1 |
| Shock Lead 200 Hz | | 2 | 2 |
| Shock Lead 400 Hz | | 1 | 1 |
| Utility 8 bit | | 2 | 2 |
| Utility 12 bit | | 1 | 1 |
| Evoked Response 8 bit | | 2 | 2 |
| Evoked Response 12 bit | | 1 | 1 |
| Accelerometer Raw Data | | 1 | 1 |
| Accelerometer Filtered Data | | 1 | 1 |
| MV Raw Data | | 20 | 1 |
| MV Filtered Data | | 20 | 1 |

Once the buffers 305 are configured, the buffers 405 are available for use by multiple tasks. More than one task can use the same buffer 405. For example, the data in the buffers 405 can be used for history data storage, for transmission through the telemetry circuit 240, or for a morphology comparison such as for cross channel timing (CCT) analysis. The controller 230 needs to keep track of multiple users of configured buffers 405 to control enabling and disabling sense channels. To track users, the controller 230 uses an analog control reference table. One embodiment of an analog control reference table is shown below in Table 5.

TABLE 5

Analog Control Reference Table

| Requestor ID | Buffer ID | In-Use Indicator | Hardware Code | Previous Index Value | Previous Sync Value |
|---|---|---|---|---|---|
| History ID | 1 | | | | |
| Telemetry ID | 2 | | | | |
| CCT ID | 2 | | | | |
| ... | ... | | | | |
| ... | N | | | | |
| ... | | | | | |

The table is indexed by the configured buffer ID and the requestor ID. In one embodiment, the requestor ID identifies one of six types of requesters or tasks. Three of the six types are reserved for history data collection, real-time telemetry transmission of data, and CCT. Generally, the number of requestor types and the types reserved will depend on the type of IMD. The buffer ID identifies the buffer used by the requester. The In-Use indicator indicates that the buffer is currently being used by the requester. The hardware code indicates the source of the data. The previous index value stores the last index register value read from the hardware by the requester. The previous sync value holds the last sync register value read from the hardware by the requestor.

By storing the previous index register value and the previous sync counter, the timing relationship of the data to other data can be determined by calculating the time stamp of the data. To calculate the timestamp, an offset is determined by multiplying the previous index value by the quotient of the cycles per sample and the samples per 16-bit word. This offset is then added to the previous sync value to construct the timestamp of the data. The time stamp is expressed in equation form as:

Data Timestamp=Sync Value+(Index*(CyclesPerSample/SamplesPer Word)).

Because the multiple users of a buffer can calculate a data timestamp for any particular set of data samples in a buffer, a user can access a segment of a buffer 405, track data, and release the buffer 405 without affecting other users of the buffer. When a sense channel is released, the controller 230 ensures that another requestor is not using the sense channel before the sense channel is disabled. A timestamp can also be used to mark a gap in the data or to indicate a change in the data.

Figure 5:
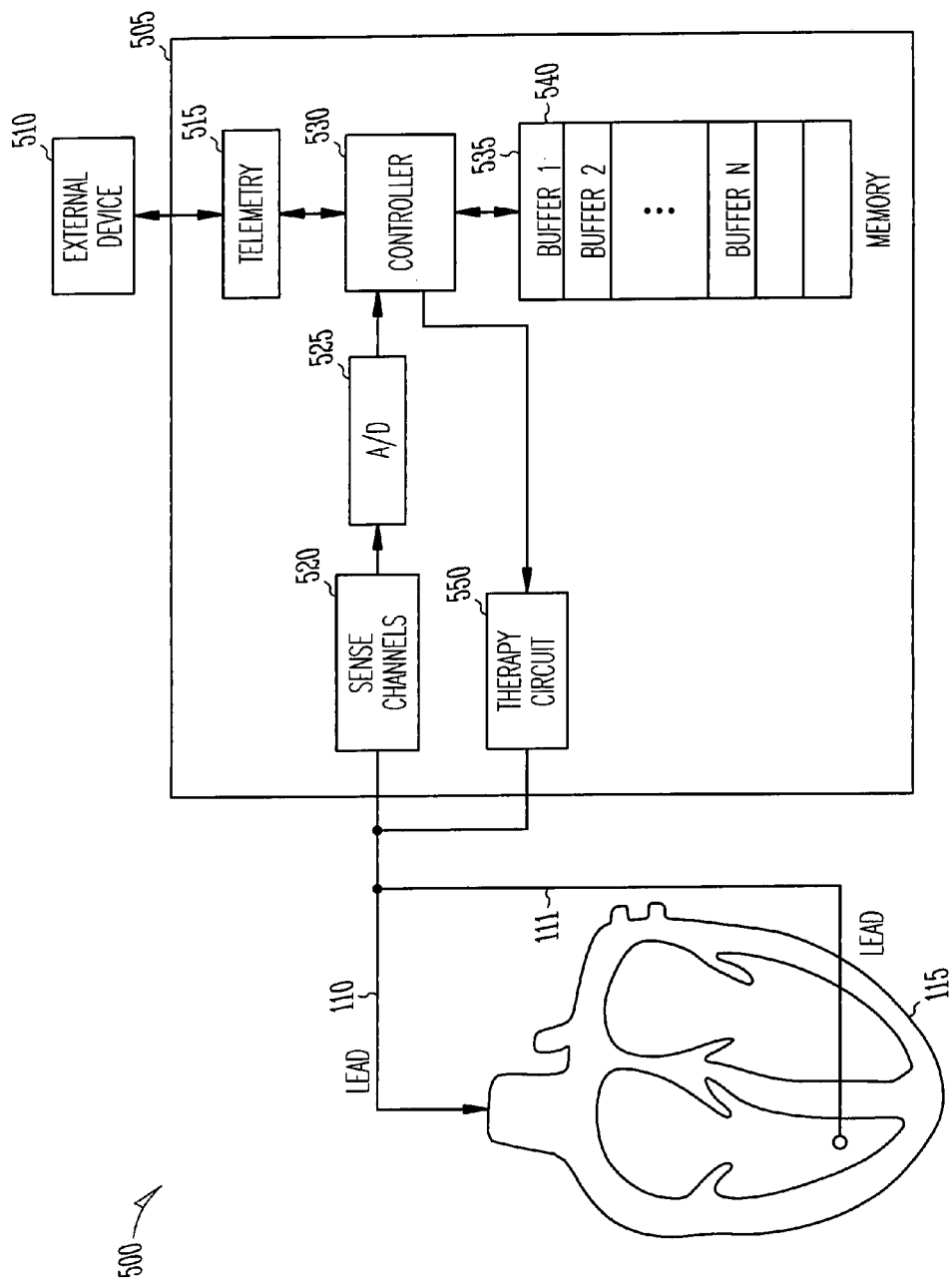
FIG. 5 is an illustration of a system comprising an implantable device and an external device.

FIG. 5 shows a system 500 able to communicate with electrical activity of a heart 115 through cardiac leads 110, 111. The system 500 includes an implanted medical device (IMD) 505 and an external device 510. The IMD 505 communicates with the external device 510 through the telemetry circuit 515. The IMD 505 includes a plurality of sense channels 520 adapted to provide analog electronic signals representative of the electrical activity of the heart 115. The IMD also includes at least one analog-to-digital (A/D) converter 525 coupled to the sense channels to convert the signals into digitized, or digital, data representative of the signals. The A/D converter 525 is coupled to a controller 530. Controller 530 initiates sampling on at least one sense channel in response to a request for data from at least one user. In one embodiment, controller 530 is a processor executing firmware. The IMD 505 also includes memory 535. The controller 530 configures a portion of the memory 535 into buffers 540 and transfers sampled sense channel data from the A/D converter 525 to a configured buffer 540. In one embodiment, the IMD 505 includes a therapy circuit 550 that provides electrical therapy to the heart 115 through the cardiac leads 110, 111.

The IMD 505 transmits data through the telemetry circuit 515 to the external device 510. The external device 510 provides requests from at least one user to the IMD 505. The external device 510 retrieves the requested data from the IMD 505. In one embodiment, the external device 510 is a programmer that can change the therapy provided. In another embodiment, the external device 510 is a clinical device capable of storing data in a database. In yet another embodiment, the data base is a patient history data base. In yet another embodiment, the external device 510 includes processing circuitry to determine patient trending and to display the trending. In yet another embodiment, the external device 510 is connected to a global computer network, such as the internet for example. In yet another embodiment, the external device 510 includes a communication module capable of transferring the data to a database accessed by a global computer network. In yet another embodiment, the external device 510 includes a wireless local area network (LAN) and communicates with the external device using the wireless LAN.

Figure 6:
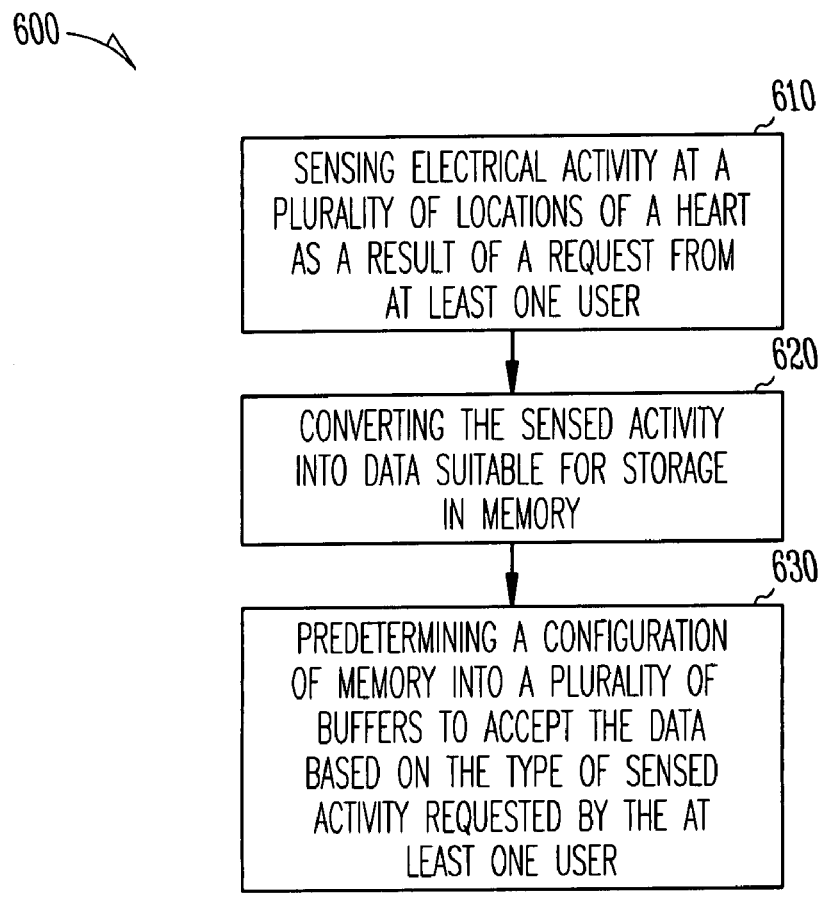
FIG. 6 illustrates a method of configuring memory to collect sensed data according to various embodiments of the present subject matter.

FIG. 6 shows a method 600 of configuring memory to collect sensed data from multiple sources. At 610, electrical activity at a plurality of locations of a heart is sensed as a result of a request from at least one user. At 620, the sensed activity is converted into data suitable for storage in memory. At 630, a configuration of memory into a plurality of buffers is predetermined to accept the data based on a number of requests and types of sensed activity requested by the user.

Although specific examples have been illustrated and described herein, it will be appreciated by those of ordinary skill in the art that any arrangement calculated to achieve the same purpose could be substituted for the specific example shown. This application is intended to cover any adaptations or variations of the present invention. Therefore, it is intended that this invention be limited only by the claims and their legal equivalents.

What is claimed is:

1. A device comprising:
    a plurality of implantable electrodes, the electrodes to sense electrical activity of a heart; and
    an implantable medical device coupled to the electrodes, the implantable medical device including:
        a plurality of sense amplifiers coupled to the electrodes, the sense amplifiers to produce analog electronic signals representative of the electrical activity;
        a programmable sampler coupled to the sense amplifiers;
        a controller coupled to the programmable sampler, wherein the controller programmably enables the sampler to selectively sample the electronic signals; and
        configurable memory coupled to the controller for storage of the sample values, wherein the memory is configurable into a number of buffers by the controller based on the programmable sampling, and wherein the memory includes a buffer length table.

2. The device of claim 1, wherein the controller includes one or a combination of hardware, software and firmware to configure memory by programmably determining a number of buffers and sizes of the buffers based on types of sensed electrical activity sampled.

3. The device of claim 2, wherein each configured buffer includes:
    a starting address register to store a starting memory address for the buffer;
    a length register to store a configured size of the buffer; and
    a control register to indicate a type of sense activity data provided to the buffer.

4. The device of claim 3, wherein each configured buffer includes a synchronization register to store a representation of time to indicate a relationship among the data stored in the plurality of configured buffers.

5. The device of claim 4, wherein each buffer further includes an index register to indicate a location within the buffer to write data.

6. The device of claim 3, wherein a type of sensed electrical activity determines a rate at which data is sampled on the sense amplifier and the size of the configured buffer.

7. The device of claim 3, wherein at least one user requests a rate at which an electronic signal is sampled, and the controller configures the size of a buffer based on the requested rate.

8. The device of claim 3, wherein the buffer is a circular buffer and further includes a rollover indicator.

9. The device of claim 3, wherein the device further includes at least one analog-to-digital (A/D) converter coupled to the sense amplifiers to convert the analog electronic signals into digital data representative of the signals.

10. The device of claim 9, wherein the A/D converter further includes a digital signal processor (DSP).

11. The device of claim 10, wherein the data representative of the signals is filtered before transfer to the buffers.

12. The device of claim 11, wherein the buffer stores filtered data sampled from an accelerometer.

13. The device of claim 3, wherein the memory further includes a channel configuration table, the table containing definitions of types of sensed electrical signals and wherein the type of signal sensed defines the size of buffers.

14. The device of claim 13, wherein the type of sensed electrical signal is an electrogram from an atrium.

15. The device of claim 13, wherein the type of sensed electrical signal is an electrogram from a ventricle.

16. The device of claim 13, wherein the plurality of sense amplifiers further includes a sense amplifier in communication with an accelerometer.

17. The device of claim 13, wherein the type of sensed electrical signal is an unfiltered signal from an accelerometer.

18. The device of claim 13, wherein the type of sensed electrical signal is minute volume.

19. The device of claim 3, wherein the memory further includes a reserved lead configuration table.

20. The device of claim 3, wherein a default buffer length table defines buffer lengths at system reset.

21. The device of claim 1, wherein at least one electrode is in communication with a high energy defibrillation lead.

22. The device of claim 1, further comprising a telemetry circuit in communication with the controller and an external device, wherein the controller transmits data from the configurable buffers to the external device.

23. The device of claim 22, wherein buffer lengths are configured based on a transmission rate of the telemetry link and a rate at which data is sampled from the sense amplifiers.

24. A device comprising:
    a plurality of implantable electrodes, wherein at least one electrode is coupled to an implantable lead; and
    an implantable pulse generator coupled to the electrodes and at least one lead, the pulse generator including:
        a plurality of sense amplifiers coupled to the electrodes, the sense amplifiers adapted to sense electrical activity of a heart and produce analog electronic signals representative of the activity;
        at least one analog-to-digital (A/D) converter coupled to the sense amplifiers to convert the signals into digital data representative of the signals;
        a controller coupled to the A/D converter wherein the controller samples data provided by the sense channels, and wherein the controller initiates sampling at least one electronic signal in response to at least one request for data from at least one user; and
        memory coupled to the controller, wherein the controller programmably configures memory into a reserved configuration of buffers based on a lead configuration of the implantable pulse generator, and wherein the memory includes a buffer length table.

25. The device of claim 24, wherein the reserved configuration is contained in a look-up table and wherein the buffers are configured according to the look-up table at system reset.

26. The device of claim 25, wherein the reserved configuration is defined based on a priority given to the sense channels.

27. The device of claim 26, wherein the priority is based on a rate at which data is being collected.

28. The device of claim 24, wherein data is collected at a rate selectable from among 100 Hertz (Hz), 200 Hz and 400 Hz.

29. A method comprising
sensing electrical activity at a plurality of locations of a heart as a result of requests from at least one user;
converting the sensed activity into data suitable for storage in memory; and
programmably configuring a memory included in an implantable medical device into a plurality if buffers and a buffer length table, wherein the buffers accept the data based on a number of requests and types of sensed activity requested by the at least one user.

30. The method of claim 29, wherein programmably configuring a memory into buffers includes:
determining lengths and starting addresses for the buffers from types of data to be collected;
indicating the types of data to be collected in the buffers; and
determining timestamps for the buffers to indicate a time relationship among the data stored in the plurality of buffers.

31. The method of claim 30, wherein programmably configuring a memory into buffers includes determining pointer values to buffer locations.

32. The method of claim 29, wherein the request includes electrogram history data to be stored.

33. The method of claim 29, wherein the request includes real time electrograms to be sent over a telemetry link.

34. The method of claim 29, wherein the request includes sensed electrical activity for a morphology comparison.

35. The method of claim 29, wherein the request includes the sensed unfiltered electrical activity of an accelerometer.

36. The method of claim 29, wherein the request includes the sensed filtered electrical activity of an accelerometer.

37. The method of claim 29, wherein the request includes the sensed electrical activity of an evoked response.

38. The method of claim 29, wherein the request includes the sensed electrical activity at a defibrillation lead.

39. The method of claim 29, wherein the request includes minute ventilation data.

40. The method of claim 29, wherein the request includes that data be sampled within a range from 100 Hertz (Hz) to 400 Hz.

41. A system in communication with electrical activity of a heart, the system comprising:
an implantable medical device, wherein the implantable device includes:
a plurality of sense channels adapted to provide analog electronic signals representative of the electrical activity;
at least one analog-to-digital (A/D) converter coupled to the sense channels to convert the signals into digital data representative of the signals;
a controller coupled to the A/D converter wherein the controller samples data provided by the sense channels, and wherein the controller initiates sampling at least one sense channel in response to a request for data from at least one user;
memory coupled to the controller, wherein the controller predetermines a configuration of a portion of the memory, the configuration including a number of buffers and sizes of buffers, to transfer sampled sense channel data from the at least one A/D converter to a configured buffer; and wherein the memory includes a buffer length table; and
a telemetry circuit coupled to the controller to transmit data; and
an external device to communicate with the implantable device, wherein the external device provides requests from at least one user to the implantable medical device, the request to sense types of electrical activity, and wherein the external device retrieves the requested data from the implantable medical device.

42. The system of claim 41, wherein each configured buffer includes:
a length register to store a configured size of the buffer;
a synchronization register to store a representation of a time to indicate a relationship among data stored in a plurality of configurable buffers; and
a control register to indicate a type of sense channel providing data to the buffer.

43. The system of claim 42, wherein the implantable medical device is a pulse generator.

44. The system of claim 43, further including at least one electrode adapted to sense electrical signals related to activity of a heart and to deliver electrical therapy to a heart.

45. The system of claim 44, wherein the implantable medical device further includes a therapy circuit coupled to the at least one electrode to deliver electrical therapy to the heart.

46. The system of claim 45, wherein the system further includes at least one sensor to provide electrical signals representative of physical activity of a patient.

47. The system of claim 41, wherein the at least one sensor includes an accelerometer.

48. The system of claim 41, further comprising processing circuitry in communication with the external device, the processing circuitry to trend the requested data and to provide data to display trending of the data retrieved from the implantable medical device.

49. The system of claim 41, wherein the external device includes a communication module to transfer the requested data retrieved from the implantable medical device to storage in a database.

50. The system of claim 49, wherein the database is suitable to be accessed via a global computer network.

51. The system of claim 50, wherein the external device includes a wireless local area network (LAN), and the external device communicates with the implantable pulse generator with the wireless LAN.

52. The system of claim 51, wherein the external device is connected to a global computer network.

* * * * *

UNITED STATES PATENT AND TRADEMARK OFFICE
CERTIFICATE OF CORRECTION

PATENT NO. : 7,286,872 B2  Page 1 of 1
APPLICATION NO. : 10/680731
DATED : October 23, 2007
INVENTOR(S) : Kramer et al.

It is certified that error appears in the above-identified patent and that said Letters Patent is hereby corrected as shown below:

In column 11, line 19, in Claim 29, delete "if" and insert -- of ---, therefor.

In column 12, line 11, in Claim 41, delete "buffer;" and insert -- buffer, --, therefor.

Signed and Sealed this

First Day of April, 2008

JON W. DUDAS
*Director of the United States Patent and Trademark Office*